Figure 1:
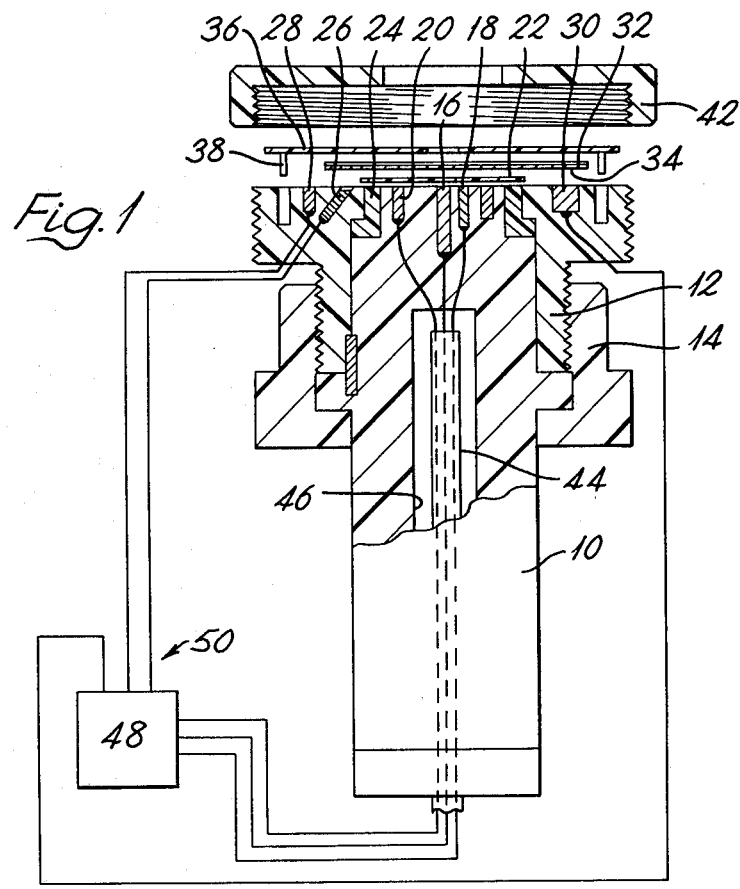

United States Patent [19]
Albery

[11] 4,377,446
[45] Mar. 22, 1983

[54] CARBON DIOXIDE MEASUREMENT

[75] Inventor: Wyndham J. Albery, London, England

[73] Assignee: National Research Development Corporation, London, England

[21] Appl. No.: 368,812

[22] Filed: Apr. 15, 1982

[30] Foreign Application Priority Data

Apr. 30, 1981 [GB] United Kingdom ............... 8113365

[51] Int. Cl.$^3$ ............................................. G01N 27/46
[52] U.S. Cl. .............................. 204/1 T; 204/195 P
[58] Field of Search .................. 204/1 P, 1 K, 195 P

[56] References Cited

U.S. PATENT DOCUMENTS

| | | | |
|---|---|---|---|
| 3,272,725 | 9/1966 | Garst | 204/1 P |
| 3,454,485 | 7/1969 | Hauk et al. | 204/1 P |
| 3,510,420 | 5/1970 | Mills | 204/195 P |
| 3,673,069 | 6/1972 | Niedrach et al. | 204/195 P |
| 3,708,412 | 1/1973 | Lofgren | 204/195 P |
| 3,719,576 | 3/1973 | Macur | 204/195 P |
| 4,268,370 | 5/1981 | Neti et al. | 204/1 P |

OTHER PUBLICATIONS

Electrochemistry of Carbon Dioxide in Dimethyl Sulfoxide at Gold and Mercury Electrodes, Haynes and Sawyer, Analytical Chemistry, pp. 332–338.
Journal of Electroanalytical Chemistry, Voltammetric Determination of Carbon Dioxide using Dimethylsulfoxide as a Solvent, Roberts and Sawyer, J. Electroanal. Chem., 9 (1965), pp. 1–7.

*Primary Examiner*—T. Tung
*Attorney, Agent, or Firm*—Cushman, Darby & Cushman

[57] ABSTRACT

Carbon dioxide in the presence of oxygen is sensed by passage of the gas mixture through a layer of polymeric material and through a first, porous, working electrode in contact with a layer of aqueous electrolyte any oxygen being reduced at the electrode; any $CO_2$ gas passes through the aqueous electrolyte and through a $CO_2$-permeable layer of polymeric material to a layer of non-aqueous solvent in contact with a second working electrode at which any $CO_2$ gas is reduced, causing a current to flow.

6 Claims, 2 Drawing Figures

CARBON DIOXIDE MEASUREMENT

This invention relates to the electrochemical measurement of carbon dioxide in a fluid which may contain oxygen.

It is known to sense carbon dioxide by electrochemical methods such as polarography. In J. Electroanal. Chem. 9, 1965 pp 1 to 7 in a report by J. L. Roberts and D. T. Sawyer, and in Anal. Chem. 39 (3), 1967 pp 332 to 338, in a report by L. V. Haynes and D. T. Sawyer, the concentration of $CO_2$ is measured by reduction at a stationary electrode in dimethylsulphoxide, and analysis of the cyclic voltammagram. However, it was essential to exclude oxygen, because oxygen is more easily reduced than $CO_2$. The almost universal presence of oxygen in normal circumstances means that such a method is not generally applicable. The present invention provides an electrochemical sensor for detecting $CO_2$ even in the presence of oxygen.

According to the invention, apparatus for sensing the presence of carbon dioxide in a fluid which may contain oxygen comprises in series array:
a first layer of high polymeric material which is permeable to carbon dioxide and oxygen, and which has in contact with one surface a porous layer of metal which constitutes a first working electrode;
in contact with said first working electrode a layer of an aqueous electrolyte;
a second layer of a high polymeric material which is permeable to carbon dioxide;
in contact with said second layer a layer of a non-aqueous solvent;
a second working electrode in contact with the non-aqueous solvent;
and circuit means arranged to hold the first working electrode at a potential such that oxygen but not carbon dioxide is reduced in the aqueous electrolyte, to hold the second working electrode at a potential such that carbon dioxide is reduced in the non-aqueous solvent, and to sense any current flowing through the second electrode.

The first working electrode may be in the form of a metallised membrane of a high polymeric material. The non-aqueous solvent may be dimethylsulphoxide (DMSO).

Usually the potentials of the first and second working electrodes are held constant with respect to first and second reference electrodes in contact with the aqueous electrolyte and the DMSO respectively. The currents generated in the aqueous solution by reduction of any oxygen present and in the DMSO by reduction of any carbon dioxide present flow through first and second counter electrodes in contact with the respective electrolytes.

Preferably the first working electrode is of larger area than the second working electrode, and the diffusion of the gases in the fluid under test is restricted to ensure that all of the oxygen passing through the first polymeric layer to the first working electrode is reduced at that electrode. The restriction may be in the form of an aperture of area less than the area of the first working electrode.

Figure 2:
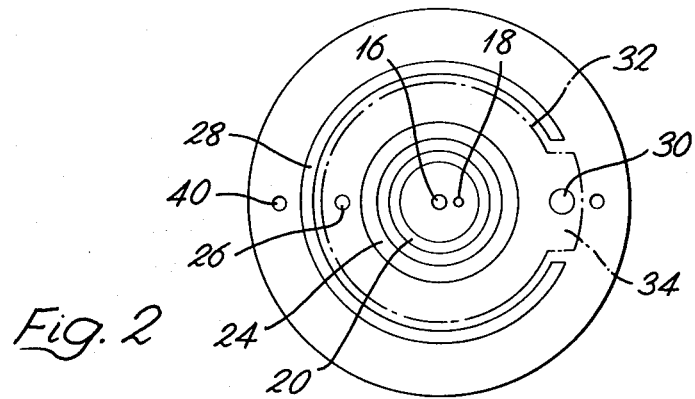

The invention will now be described by way of example only with reference to the accompanying drawings in which:

FIG. 1 is a gas sensor according to the invention shown partly in longitudinal section and partly exploded; and
FIG. 2 is a plan view of the sensor electrodes.

In FIG. 1, a sensor body has an inner part 10 and an outer part 12 held together by a nut 14. The upper faces of both the inner and outer parts are coplanar, and six electrodes or electrode contacts are recessed to lie flush with the coplanar surfaces.

Referring to both FIGS. 1 and 2, in the inner part 10 are a central second working electrode 16 in the form of a gold or silver rod, and an adjacent silver/silver chloride reference electrode 18 both surrounded by a silver counter electrode 20. A circular membrane 22 of high polymeric material covers the electrodes 16, 18, 20 and is also supported by a washer 24 around the outside of the inner body 10. Between the membrane 22 and the electrodes is a thin layer (not illustrated) of dimethylsulphoxide.

The coplanar surface of the outer body 12 carries a silver/silver chloride reference electrode 26 and a silver counter electrode 28 which is "C" shaped. Between the arms of the "C" there is a silver epoxy stud 30, and above the membrane 22 is a metallised membrane electrode 32, the lower surface of which is covered with a layer of sputtered gold 34. The gold layer is largely circular, of diameter smaller than the counter electrode 28, but with an extension coinciding with the aperture between the arms of electrode 28 to make contact with the stud 30.

Between the metallised membrane 32 and the membrane 22 is a thin layer (not illustrated) of aqueous electrolyte.

Above the membrane electrode 32 is a circular washer 36 which has location pins 38 which can enter depressions 40 in the upper surface of the outer body 12. When the washer 36 is held in position by a screw cap 42, the metallised membrane 32 is pressed towards the membrane 22, part of the metallised surface of membrane 32 being held in contact with the stud 30, and the membrane 22 is pressed towards the washer 24. The thin layers of aqueous electrolyte and of DMSO remain between the membranes and the membrane 22 and body 10 respectively.

The screw cap has a central aperture, and the washer 36 has a smaller central aperture through both of which an atmosphere or fluid can pass to reach the upper, unmetallised surface of the membrane electrode 32.

Wire contacts to the electrodes 16, 18 and 20, which are the carbon dioxide sensing electrodes, pass through a cable 44 in a cylindrical aperture 46 within the inner body 10 to a measuring and control circuit 48. Wire contacts to the electrodes 26, 28 and electrode contact 30 pass through the outer body 12 to the circuit 48. The electrodes 26, 28 and the metallised membrane electrode 32 are the oxygen removal electrodes. The circuit 48 is arranged to hold the first working electrode, i.e. membrane electrode 32, at a potential at which oxygen is reduced but carbon dioxide is not, and to hold the second working electrode 16 at a potential at which carbon dioxide is reduced, and to sense any current flowing between electrode 16 and the counter electrode 20. The potentials are held constant with respect to the respective reference electrodes 18, 26.

In operation, an atmosphere or fluid under test passes through the apertures in the screw cap 42 and washer 36 to the metallised membrane electrode 32. Oxygen and carbon dioxide gas pass through the membrane 32 and through the metallised layer to the aqueous electrolyte at which oxygen is reduced. The reduction current is proportional to the oxygen concentration and is measured by the circuit 48. Carbon dioxide gas passes through the aqueous electrolyte and through the membrane 22 to the DMSO layer in contact with the second working electrode 16 at which the $CO_2$ gas is reduced. This produces a current proportional to the $CO_2$ concentration, which is measured by the circuit 48.

Typically the metallised membrane electrode 32 is a layer of "Teflon" (Registered Trade Mark) 12 microns thick and covered with a sputtered layer of gold. The aqueous electrolyte is buffered to a pH of 5 with potassium hydrogen phthalate and the metal layer of the membrane electrode is held at a potential of $-0.6$ volts. The membrane 22 is typically a layer of "Teflon" (Registered Trade Mark) 12 microns thick, and the second working electrode 16 is held at a potential of $-2.3$ volts.

Alternatively, the metallised membrane electrode may be prepared by painting a porous membrane of "Gorotex" (Registered Trade Mark) with a gold resinate solution and heating to leave a layer of gold.

As an alternative to silver, the second working electrode 16 may be made of mercury, nickel, gold, lead or glassy carbon.

A carbon dioxide sensor according to the invention may have a response time as fast as 5 seconds to a 90% concentration of carbon dioxide. Concentrations as low as 0.1% of $CO_2$ may be detected, and the sensor is suitable for use in medical applications, when both oxygen and carbon dioxide concentrations can be measured.

I claim:

1. Apparatus for sensing the presence of carbon dioxide in a fluid which may contain oxygen comprises in series array:
    a first layer of high polymeric material which is permeable to carbon dioxide and oxygen, and which has in contact with one surface a porous layer of metal which constitutes a first working electrode;
    in contact with said first working electrode a layer of an aqueous electrolyte;
    a second layer of high polymeric material which is permeable to carbon dioxide;
    in contact with said second layer a layer of a non-aqueous solvent;
    a second working electrode in contact with the non-aqueous solvent;
    and circuit means arranged to hold the first working electrode at a potential such that oxygen but not carbon dioxide is reduced in the aqueous electrolyte, to hold the second working electrode at a potential such that carbon dioxide is reduced in the non-aqueous solvent, and to sense any current flowing through the second working electrode.

2. Apparatus according to claim 1 in which the first working electrode is a metallised membrane of a high polymeric material.

3. Apparatus according to claim 1 in which the non-aqueous solvent is dimethylsulphoxide.

4. Apparatus according to claim 1 further comprising a first reference electrode in contact with the aqueous electrolyte; means for maintaining the potential of the first working electrode constant with respect to the first reference electrode; a first counter electrode in contact with the aqueous electrolyte; a second reference electrode in contact with the non-aqueous electrolyte; means for maintaining the potential of the second working electrode constant with respect to the second reference electrode; and a second counter electrode in contact with the non-aqueous electrolyte; currents corresponding to the reduction of any oxygen and any carbon dioxide present in the fluid flowing respectively through the first and second counter electrodes.

5. Apparatus according to claim 1 in which the first working electrode is of larger area than the second working electrode, and there is further provided a restriction to restrict access of the fluid to the first high polymeric layer.

6. A method of sensing the presence of carbon dioxide in a fluid which may contain oxygen comprises:
    exposing to the fluid a first layer of high polymeric material which is permeable to carbon dioxide and oxygen, and which has in contact with one surface a porous layer of metal which constitutes a first working electrode, the first working electrode being in contact with a layer of an aqueous electrolyte remote from the fluid;
    holding the first working electrode at a potential such that oxygen but not carbon dioxide is reduced in the aqueous electrolyte;
    exposing to the aqueous electrolyte a second layer of a high polymeric material which is permeable to carbon dioxide, the second layer of high polymeric material being in contact with a layer of a non-aqueous solvent remote from the aqueous solvent, and there being a second working electrode in contact with the non-aqueous solvent;
    holding the second working electrode at a potential such that carbon dioxide is reduced in the non-aqueous solvent;
    and sensing any current flowing through the second working electrode.

* * * * *